(12) United States Patent
deBeer

(10) Patent No.: US 6,562,064 B1
(45) Date of Patent: May 13, 2003

(54) PLACEMENT CATHETER ASSEMBLY

(75) Inventor: Nicholas C. deBeer, Burlingame, CA (US)

(73) Assignee: Vascular Architects, Inc., San Jose, CA (US)

( * ) Notice: Subject to any disclaimer, the term of this patent is extended or adjusted under 35 U.S.C. 154(b) by 0 days.

(21) Appl. No.: 09/703,984

(22) Filed: Oct. 27, 2000

(51) Int. Cl.$^7$ ................................................ A61F 2/06
(52) U.S. Cl. .................... 623/1.12; 623/1.11; 623/1.23; 606/108
(58) Field of Search .............................. 623/1.11, 1.12, 623/1.22, 1.23; 606/108, 191, 198

(56) References Cited

U.S. PATENT DOCUMENTS

| | | | |
|---|---|---|---|
| 4,969,890 A | 11/1990 | Sugita et al. | |
| 5,279,596 A | * 1/1994 | Castaneda et al. | 604/282 |
| 5,372,600 A | 12/1994 | Beyar et al. | |
| 5,441,516 A | * 8/1995 | Wang et al. | 606/198 |
| 5,476,505 A | 12/1995 | Limon | |
| 5,562,641 A | * 10/1996 | Flomenblit et al. | 604/281 |
| 5,571,089 A | * 11/1996 | Crocker | 604/102 |
| 5,772,668 A | 6/1998 | Summers et al. | |
| 5,776,142 A | 7/1998 | Gunderson | |
| 5,782,838 A | * 7/1998 | Sugimura et al. | 606/108 |
| 5,788,707 A | * 8/1998 | Del Toro et al. | 606/108 |
| 5,797,952 A | * 8/1998 | Klein | 606/198 |
| 5,810,871 A | 9/1998 | Tuckey et al. | |
| 6,027,516 A | 2/2000 | Kolobow et al. | |
| 6,090,115 A | * 7/2000 | Beyar et al. | 606/113 |
| 6,238,430 B1 | * 5/2001 | Klumb et al. | 623/1.11 |
| 6,280,465 B1 | * 8/2001 | Cryer | 623/1.11 |
| 6,346,118 B1 | * 2/2002 | Baker et al. | 623/1.12 |
| 6,451,025 B1 | * 9/2002 | Jervis | 606/108 |

OTHER PUBLICATIONS

Pub. No. US 2002/0007206 A1, published Jan. 17, 2002, Bui et al., Stent Delivery System.*

* cited by examiner

Primary Examiner—Corrine McDermott
Assistant Examiner—Cheryl Miller
(74) Attorney, Agent, or Firm—James F. Hann; Haynes Beffel & Wolfeld LLP

(57) ABSTRACT

An embodiment of a placement catheter assembly (2) comprises an inner shaft (10) movably housed within a hollow outer shaft (8). A radially-expansible endoluminal prosthesis (6) is mounted about the inner shaft between the distal ends of the inner and outer shafts. Distal and proximal end release elements (22/28, 16/34), such as pull wires, are carried by the inner and outer shafts and releasably secure the prosthesis to the inner and outer shafts. The prosthesis in the radially contracted state and the distal and proximal end release elements together have a maximum diameter which is at most about equal to the diameter of the distal part (48) of the outer shaft to facilitate placement of the prosthesis.

12 Claims, 2 Drawing Sheets

PLACEMENT CATHETER ASSEMBLY

CROSS-REFERENCES TO RELATED APPLICATIONS

This is related to this patent application Ser. No. 09/258,542 filed Feb. 26, 1999 and entitled Catheter with Controlled Release Endoluminal Prosthesis, now U.S. Pat. No. 6,248,122 and U.S. patent application Ser. No. 09/400,952 filed Sep. 22, 1999 and entitled Catheter Assembly with Controlled Release Endoluminal Prosthesis and Method for Placing, now U.S. Pat. No. 6,238,430.

STATEMENT AS TO RIGHTS TO INVENTIONS MADE UNDER FEDERALLY SPONSORED RESEARCH AND DEVELOPMENT

None

BACKGROUND OF THE INVENTION

The present invention provides devices for the endoluminal placement of prostheses, particularly within the vascular system for the treatment of peripheral and cardiovascular disease, such as vascular stenoses, dissections, aneurysms, and the like. The apparatus, however, are also useful for placement in other body lumens, such as the ureter, urethra, biliary tract, gastrointestinal tract, trachea and the like, for the treatment of other conditions which may benefit from the introduction of a reinforcing or protective structure within the body lumen. The prostheses will be placed endoluminally. As used herein, "endoluminally" will mean placement by percutaneous or cutdown procedures, wherein the prosthesis is translumenally advanced through the body lumen from a remote location to a target site in the lumen. In vascular procedures, the prostheses will typically be introduced "endovascularly" using a catheter over a guidewire under fluoroscopic guidance. For vascular applications the catheters and guidewires may be introduced through conventional access sites to the vascular system, such as through the femoral artery, or brachial and subclavian arteries, for access to the target site.

An endoluminal prosthesis typically comprises at least one radially expansible, usually cylindrical, body segment. By "radially expansible," it is meant that the body segment can be converted from a small diameter configuration (used for endoluminal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. Alternatively, the prosthesis can be self-expanding. Such self-expanding structures are provided by a temperature-sensitive superelastic material, such as Nitinol, which naturally assumes a radially expanded condition once an appropriate temperature has been reached. The appropriate temperature can be, for example, a temperature slightly below normal body temperature; if the appropriate temperature is above normal body temperature, some method of heating the structure must be used. Another type of self-expanding structure uses resilient material, such as a stainless steel or superelastic alloy, and forming the body segment so that it possesses its desired, radially-expanded diameter when it is unconstrained, e.g., released from radially constraining forces a sheath. To remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well-known in the art and do not comprise part of the present invention.

The dimensions of a typical endoluminal prosthesis will depend on its intended use. Typically, the prosthesis will have a length in the range from 0.25 cm to 10 cm, usually being from about 0.8 cm to 5 cm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 30 mm, preferably being in the range from about 3 mm to 15 mm for vascular applications.

One type of endoluminal prosthesis includes both a stent component and a graft component. These endoluminal prostheses are often called stent grafts. A stent graft is typically introduced using a catheter with both the stent and graft in contracted, reduced-diameter states. Once at the target site, the stent and graft are expanded. After expansion, the catheter is withdrawn from the vessel leaving the stent graft at the target site.

Grafts are used within the body for various reasons, such as to repair damaged or diseased portions of blood vessels such as may be caused by injury, disease, or an aneurysm. It has been found effective to introduce pores into the walls of the graft to provide ingrowth of tissue onto the walls of the graft. With larger diameter grafts, woven graft material is often used. In small diameter vessels, porous fluoropolymers, such as PTFE, have been found useful.

Coil-type stents can be wound about the catheter shaft in torqued compression for deployment. The coil-type stent can be maintained in this torqued compression condition by securing the ends of the coil-type stent in position on a catheter shaft. The ends are released by, for example, pulling on wires once at the target site. See, for example, U.S. Pat. Nos. 5,372,600 and 5,476,505. Alternatively, the endoluminal prosthesis can be maintained in its reduced-diameter condition by a sleeve; the sleeve can be selectively retracted to release the prosthesis. A third approach is the most common. A balloon is used to expand the prosthesis at the target site. The stent is typically extended past its elastic limit so that it remains in its expanded state after the balloon is deflated and removed. One balloon expandable stent is the Palmaz-Schatz stent available from the Cordis Division of Johnson & Johnson. Stents are also available from Medtronic of Santa Rosa, Calif. and Guidant Corporation of Indianapolis, Ind.

SUMMARY OF THE INVENTION

The present invention is directed to a placement catheter assembly which facilitates placement of an endoluminal prosthesis by reducing the maximum size of the endoluminal prosthesis during placement. The present invention finds particular utility for the percutaneous insertion of an endoluminal prosthesis.

The placement catheter assembly, according to one embodiment, comprises a hollow outer shaft and an inner shaft movably housed within the outer shaft. A radially-expansible endoluminal prosthesis is mounted about the inner shaft between the distal ends of the inner and outer shafts. A distal end attachment device comprises a distal end release element, such as a pull wire, which is carried by the inner shaft and releasably secures the prosthesis to the inner shaft. A proximal end attachment device comprises a proximal end release element, also typically a pull wire, which is carried by the outer shaft and releasably secures the prosthesis to the outer shaft. The prosthesis in the radially contracted state and the distal and proximal end release elements together have a maximum diameter which is at most about equal to the diameter of the distal part of the outer shaft to facilitate placement of the prosthesis.

Several advantages may be realized by various embodiments of the present invention. In particular, the invention may permit the user to access smaller vessels and may require smaller access sites resulting in shorter incisions, less pain for the patient and quicker healing. The use of smaller diameters may help to reduce or eliminate disruption to plaque at a target site. Limiting the diameter of the device may help to, in general, reduce complications arising from the procedure.

Other features and advantages of the invention will appear from the following description in which the preferred embodiment has been set forth in detail in conjunction with the accompanying drawings.

DESCRIPTION OF THE SPECIFIC EMBODIMENTS

Figure 1:
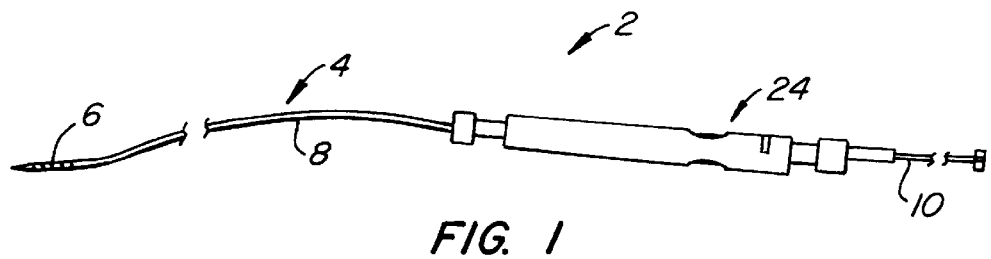
FIG. 1 is an overall view of a placement catheter assembly made according to the invention.
Figure 2:
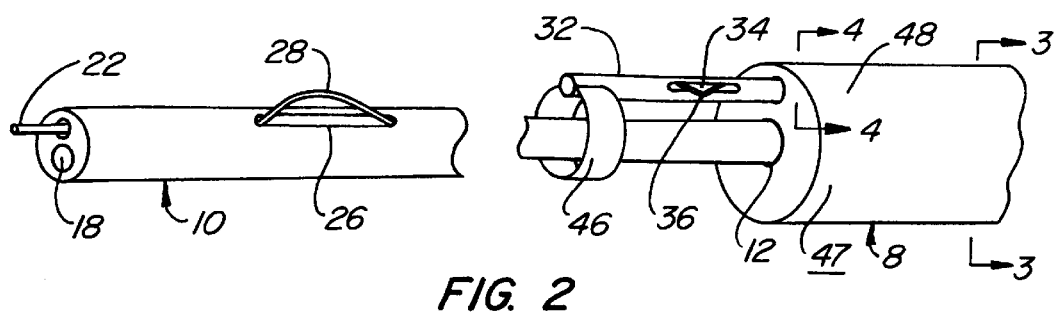
FIG. 2 is an enlarged, isometric view of the distal end placement catheter of FIG. 1 with the stent graft removed for clarity of illustration.
Figure 3:
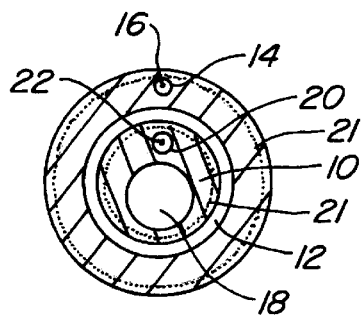
FIG. 3 is a cross-sectional view taken along line 3—3 of FIG. 2.
Figure 6:
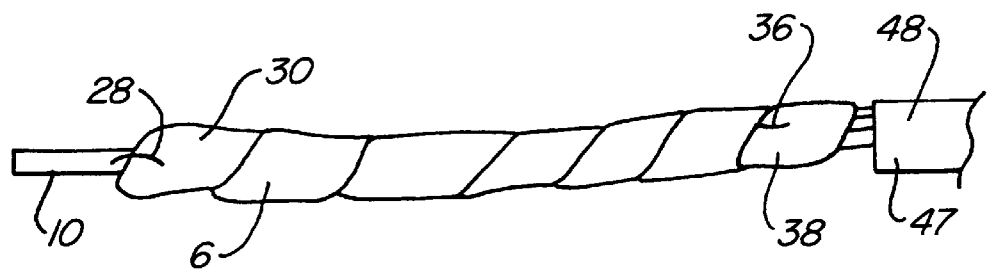
FIG. 6 is an enlarged view of the stent graft of FIG. 1 in a radially contracted state.
Figure 7:
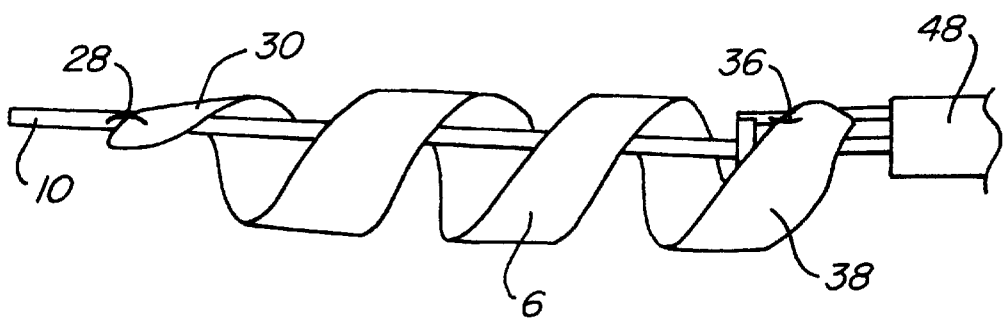
FIG. 7 is a view similar to FIG. 6, but after having rotated the inner shaft relative to the outer shaft, thus placing the stent graft in a radially expanded state.

FIG. 1 illustrates a placement catheter assembly 2 comprising a placement catheter 4 to which a radially expandable coiled stent graft 6 is mounted. Examples of stent grafts are disclosed in published PCT patent application Nos. U.S. 00/05043 and U.S. 00/05310. Other types of endoluminal prostheses may be used instead of coiled stent graft 6. Referring now also to FIGS. 2 and 3, placement catheter 4 is seen to include a dual lumen outer shaft 8 and a dual lumen inner shaft 10. Outer shaft 8 includes a shaft lumen 12, within which inner shaft 10 is housed, and a release element lumen 14 which houses a first pull wire 16. Inner shaft 10 defines a lumen 18 and a second release element lumen 20 housing a second pull wire 22. The construction of shafts 8 and 10 may be conventional to create an elongate, flexible placement catheter 4. The catheter shafts typically have sufficient torsional rigidity to permit stent graft 6, or some other coiled endoluminal prosthesis, to be placed in its radially contracted state as shown in FIG. 6 and in its radically expanded state as shown in FIG. 7. For example, outer shaft 8 and inner shaft 10 may each be of a braided type, such as one made of Pebax or nylon with a layer of braided fibers 21, typically made of stainless steel, embedded therein. Other materials, including metals and/or polymers, may be used to provide shafts 8, 10 with the desired torque characteristics. Lumen 18 is typically used to provide for passage of a guidewire, not shown; other uses for guidewire lumen 18 include delivering a liquid or a smaller catheter to a target site, guidance for optical imaging devices or for other therapeutic or diagnostic purposes.

Figure 8:
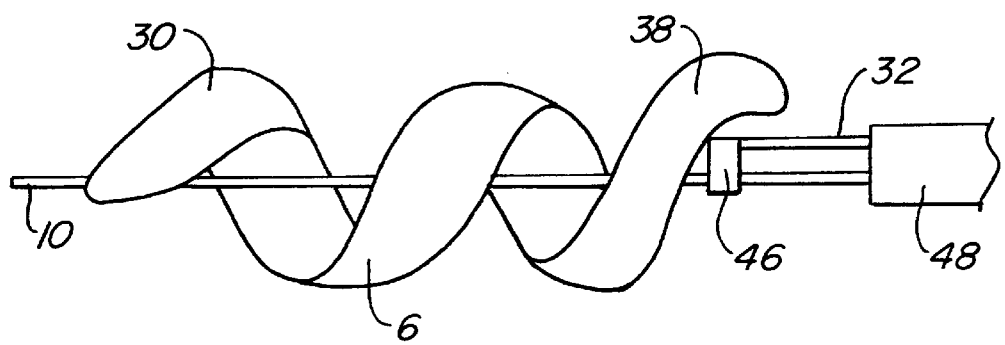
FIG. 8 is a view similar to that of FIG. 7, but after the pull wires have been pulled from the stent graft, thus releasing the distal and proximal ends of the stent graft from the assembly.

Placement catheter 4 also includes a proximal end adapter 24 from which outer and inner shafts 8 and 10 and pull wires 16 and 22 extend. A slot 26 is formed in inner shaft 10 and opens into lumen 20 to permit a portion 28 of pull wire 22 to extend outwardly from inner shaft 10 as shown in FIG. 2. Pull wire 22 is used to temporarily secure the distal end 30 of stent graft 6 to inner shaft 10 as shown in FIGS. 6 and 7. Pull wire 22, extending from proximal end adapter 24, is pulled to release distal end 30 of stent graft 6 from inner shaft 10 as is shown in FIG. 8.

Adapter 24 is preferably constructed to permit inner shaft 10 to be rotated and moved longitudinally within outer shaft 8, and to permit the user to selectively pull on pull wires 16, 22. An example of a suitable proximal end adapter is disclosed in U.S. patent application Ser. No. 09/618,974 filed Jul. 19, 2000.

Figure 4:
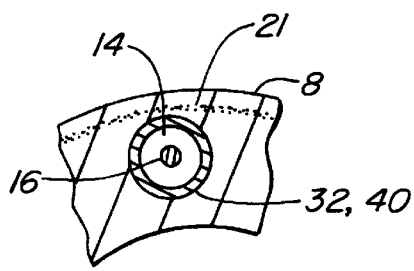
FIG. 4 is a cross-sectional view taken along line 4—4 of FIG. 2.
Figure 5:
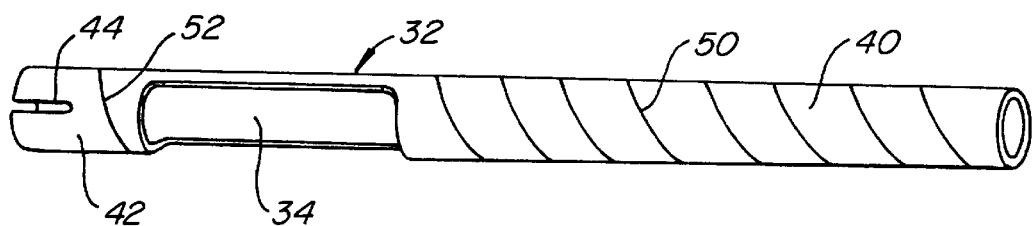
FIG. 5 is an enlarged isometric view of the pull wire holder of FIG. 2.

FIGS. 2, 4 and 5 illustrate a pull wire holder 32 in the form of a section of hypotube having a side slot 34 from which a portion 36 of first pullwire 16 can extend and engage the proximal end 38 of stent graft 6. See FIGS. 6 and 7. Pulling on pull wire 16 at proximal end adapter 24 permits release of proximal end 38 of stent graft 6 from outer shaft 8. Holder 32 includes a proximal portion 40 secured within the distal end of lumen 14. See FIG. 4. In one embodiment holder 32 is about 2.5 cm long and has a diameter of about 0.4 mm and extends about 1.9 cm into lumen 14. Other structure and techniques for releasably securing either or both ends of stent graft 6 to placement catheter 4 may be used.

Portions 28 and 36 of pull wires 22 and 16, plus holder 32, are positioned radially inwardly of the outside surface 47 of the distal part 48 of outer shaft 8. This helps to ensure that when stent graft 6 is in the radially-contracted state of FIG. 6, stent graft 6, portions 28 and 36 and holder 32 together have a maximum diameter which is at most about equal to distal part 48.

The distal end 42 of holder 32 has a pair of slits 44 formed therein to facilitate mounting a radiopaque band 46 to end 42 so to surround inner shaft 10 as shown best in FIG. 2. While band 46 is preferably radiopaque, band 46 may be made of other remotely visualizable material. Band 46 provides the user with an accurate indication of the location of distal end 42 of pull wire holder 32. Holder 32 has a spiral cut 50 along end 40 and a single turn spiral cut 52 along end 42 to enhance the flexibility, and thus trackability, of catheter 4. While band 32 is shown as a solid cylindrical sleeve, band 32 could be, for example, a coil of a remotely visulizable material.

In use, stent graft 6 is positioned over inner shaft 10 between the distal ends of the inner and outer shafts 10 and 8. Stent graft 6 is secured to inner shaft by portion 28 of pull wire 22 while the proximal end of the stent graft is secured to outer shaft 8 by portion 36 of pull wire 16. By rotating inner shaft 10 relative to outer shaft 8, stent graft 6 can be transformed from its relatively loose, radially expanded condition of FIG. 7 to a more tightly coiled, radially contracted state of FIG. 6. Stent graft 6 may also be tightly wound onto inner shaft 10 to assume a more tightly coiled, radially contracted state. In this radially contracted state, stent graft 6 and the attachment elements, specifically portion 28 of pull wire 22, portion 36 of pull wire 16 and pull wire holder 32, have a maximum diameter which is at most about equal to the maximum diameter of the distal part 48 of outer shaft 8. This facilitates placement, especially percutaneous placement, of stent graft 6 within, typically, a blood vessel. Once in place, which is typically accomplished using a guidewire and remote visualization techniques, such as x-ray fluoroscopy, stent graft 6 may be simply released by pulling on pull wires 16, 22 one-at-a-time or simultaneously. However, to ensure the proper position and location of stent graft 6 within the hollow body structure, the user may rotate inner shaft 10 within outer shaft 8 so to move stent graft 6 from the radially contracted state of FIG. 6 to the radially expanded state of FIG. 7, at which stent graft 6 will typically be in a substantially fully expanded state touching the walls of the blood vessel or other hollow body structure. If stent graft 6 is not properly positioned, the user may rewind stent graft 6 into a tightly coiled state by reversing the rotation of inner shaft 10 to permit stent graft 6 to be repositioned. Once in a proper position, pull wires 16, 22 are pulled, thus releasing portions 28, 36 from the distal and proximal ends 30, 38 of stent graft 6, thus releasing the stent graft from placement catheter 4 as shown in FIG. 8. Placement catheter 4 is then withdrawn from the patient.

While the invention may be used within a variety of body lumens defined by hollow-body structures, it finds particular utility in vascular applications. Examples of vascular applications include peripheral vessels such as iliac, SFA and renal arteries. Other vascular applications include carotids, saphenous vein bypass grafts and coronary arteries.

Modification and variation can be made to the disclosed embodiment without departing from the subject of the invention as defined in the following claims.

Any and all patents, patent applications and printed publications referred to above are incorporated by reference herein.

What is claimed is:

1. A placement catheter assembly comprising:

a hollow outer shaft comprising a distal part, said distal part comprising a distal end;

an inner shaft, having a distal end, movably housed within the outer shaft;

a radially-expansible endoluminal prosthesis mounted about the inner shaft between the distal ends of the inner and outer shafts;

a distal end attachment device comprising a distal end release element carried by the inner shaft and releasably securing the prosthesis to the inner shaft;

a proximal end attachment device comprising:

an elongate, tubular proximal end release element holder extending axially away from the distal end of the outer shaft;

a proximal end release element carried by the outer shaft with a part of the proximal end release element passing through the holder;

the holder having a side opening from which a portion of the proximal end release element extends to engage the prosthesis thereby releasably securing the prosthesis to the outer shaft; and the prosthesis in a radially contracted state and the distal and proximal end release elements together having a maximum diameter which is at most about equal to the diameter of the distal part of the outer shaft so that placement of the prosthesis is facilitated.

2. The placement catheter assembly according to claim 1 wherein the outer shaft defines a first lumen, which houses the proximal end release element, and a second lumen, which houses the inner shaft.

3. The placement catheter assembly according to claim 2 wherein the inner shaft defines a third lumen, which houses the distal end release element, and a fourth lumen.

4. The placement catheter assembly according to claim 3 wherein said fourth lumen comprises a guidewire lumen.

5. The placement catheter assembly according to claim 2 wherein the inner shaft defines a third lumen housing the distal end release element.

6. The placement catheter assembly according to claim 5 further comprising an opening, formed in the inner shaft spaced apart from the distal end of the inner shaft, which opens into the third lumen to permit a portion of the distal end release element to extend through the opening and engage the prosthesis.

7. The placement catheter assembly according to claim 1 wherein the outer shaft defines a first lumen, which houses the proximal end release element, and a second lumen, which houses the inner shaft, a portion of the holder extending into the first lumen.

8. The placement catheter assembly according to claim 1 wherein the holder is a flexible tube.

9. The placement catheter assembly according to claim 1 further comprising a remotely visualizable band secured to the bolder, the band circumscribing the inner shaft.

10. The placement catheter assembly according to claim 1 wherein the distal and proximal end release elements comprise pull wires.

11. The placement catheter assembly according to claim 1 wherein the prosthesis is a coiled endoluminal prosthesis.

12. The placement catheter assembly according to claim 11 wherein the coiled endoluminal prosthesis is a coiled stent graft.

* * * * *